United States Patent [19]

Mangiaracina

[11] Patent Number: 5,162,541

[45] Date of Patent: Nov. 10, 1992

[54] TRANSFER HYDROGENOLYSIS OF ALKYLHETEROARYL HALO-CONTAINING COMPOUNDS

[75] Inventor: Pietro Mangiaracina, Monsey, N.Y.

[73] Assignee: Schering Corporation, Kenilworth, N.J.

[21] Appl. No.: 579,768

[22] Filed: Sep. 10, 1990

[51] Int. Cl.$^5$ .......................... C07D 233/64
[52] U.S. Cl. .................. 514/400; 548/335.5; 548/345.1
[58] Field of Search ................ 548/342, 346

[56] References Cited

FOREIGN PATENT DOCUMENTS 214058  3/1987  European Pat. Off. .
0338939 10/1989  European Pat. Off. .

OTHER PUBLICATIONS

European Journal of Medicinal Chemistry, vol. 24, pp. 259-262 (1989).
Journal of Medicinal Chemistry, vol. 13, No. 5, p. 1027 (1970).
Synthesis, pp. 91-95 (Feb. 1988).
Chem. Reviews, vol. 85 pp. 129-170 (1985).
The Journal of Medicinal Chemistry, vol. 33, No. 1, pp. 4-11 (1990).
Nature, vol. 327 pp. 117-123 (May 1987).
Chemical Abstracts, 1986 (11): 72519Z.
Arch. Pharm. (Weinheim), 313, 709-714 (1980).
Advances in the Biosciences, vol. 51 pp. 39-46, (Pergamon, Oxford, 1985).
Tetrahedron Letters, vol. 26, No. 11, 1381-1384 (1985).
Synthesis, pp. 929-932 (Nov. 1980).

Primary Examiner—Mary C. Lee
Assistant Examiner—Lenora Ava Miltenberger
Attorney, Agent, or Firm—Edward H. Mazer; James R. Nelson

[57] ABSTRACT

A method for dehalogenating a compound of the generalized structure

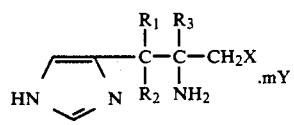

is disclosed where:

$R_1$, $R_2$ and $R_3$ independently are hydrogen or methyl or $R_1$ and $R_3$ taken together represent methylene, with the proviso that $R_1$, $R_2$ and $R_3$ are not all methyl;
X is a halogen;
m is zero, 1 or 2; and
Y is a pharmaceutically acceptable acid.

The method comprises contacting compound I with a catalytic hydrogenolysis system to replace the halogen with a hydrogen. A particularly preferred hydrogenolysis system comprises Pd/C and ammonium formate. A preferred starting material is

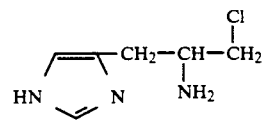

12 Claims, No Drawings

TRANSFER HYDROGENOLYSIS OF ALKYLHETEROARYL HALO-CONTAINING COMPOUNDS

BACKGROUND AND SUMMARY OF THE INVENTION

The present invention is directed at an improved method for dehalogenating halogen-containing compounds, particularly substituted alkylheteroaryl halo-compounds. More specifically, the present invention is directed at dehalogenating 4-(2 amino-3-chloropropyl) imidazole to produce α-methyl histamine.

Optically pure (R)-(−)-α-methyl histamine,

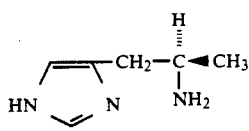

has been found to selectively agonize histamine $H_3$ receptors. See for example, *The Journal of Medicinal Chemistry* Vol. 33, No. 1 pages 4-11 (1990), and *Nature* Vol. 327 pages 117-123 (May, 1987). However, preparation of the desired optically active compound has been difficult and relatively expensive. *European Journal of Medicinal Chemistry*, Volume 24, pages 259-262 (1989) describes a process for preparing (R)- and (S)-α-methylhistamine from (R) and (S)-histidinol which included chlorination by $SOCl_2$ followed by reduction of the chloromethyl substituent with $H_2$-Pd/C. However, the reduction of the chloromethyl substituent has to be conducted under relatively high pressure (25-34 atmospheres) and a hydrogen atmosphere.

Ison and Casy in *Journal of Medicinal Chemistry*, Volume 13 No. 5, page 1027, (1970) describe a method for the production of α-methylhistamine from the dihydrobromide salt in a heated pressure vessel. However, the use of a high pressure halide reduction is not desirable because of the increased cost and safety considerations.

Ram and Ehrenkaufer in *Synthesis*, pages 91-95, (February, 1988) describe the dehalogenation of 2,4,6-trichlorophenol to phenol using ammonium formate in the presence of methanol and a palladium-on-carbon catalyst. Anwer and Spatola in *Tetrahedron Letters*, Vol. 26 No. 11, pp 1381-1384 (1985) also describe a similar method for the dehalogenation of 2,4,6-trichlorophenols.

In *Synthesis*, pages 929-932, (November, 1980) Anwer and Spatola describe a method to produce leucine-enkephalin by the rapid removal of hydrogenolysable protecting groups, such as benzyloxycarbonyl, at room temperature and under atmospheric pressure using ammonium formate and a Pd/C catalyst.

Johnston and Wilby in *Chem. Rev.* Vol. 85, pages 129-170, (1985) describe a method for heterogeneous transfer hydrogenolysis of aromatic halides using triethylammonium formate in the presence of 5% Pd/C catalyst. Table XXX shows the removal of halogen from substituted benzenes where the halogen was bonded directly to the ring or to an alkenyl substituent. There were no examples illustrating the removal of halogen from an alkyl substituent and, in particular removal of only a single halogen.

Accordingly, it would be advantageous to have a method for dehalogenating halo-containing compounds, particularly monohaloalkylheteroaryl compounds substantially completely under relatively mild conditions without significantly affecting the stereoconfiguration.

The present invention is directed at a method for dehalogenating a compound of the generalized structure

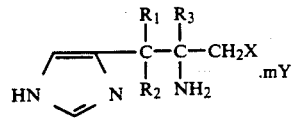

wherein $R_1$, $R_2$ and $R_3$ independently are hydrogen or methyl, or $R_1$ and $R_3$ taken together represent a methylene, with the proviso that $R_1$, $R_2$, and $R_3$ are not all methyl;

X is halogen;

m is zero, 1 or 2; and

Y is a pharmaceutically acceptable acid, comprising contacting the compound with a catalytic hydrogenolysis system to produce a compound of the structure

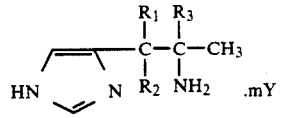

The catalytic hydrogenolysis system preferably comprises:

A. a palladium or nickel hydrogenolysis catalyst preferably supported and more preferably selected from the group consisting of Pd/C and Pd $(OAc)_2$/C; and B. a hydrogen donor selected from the group consisting of unsaturated hydrocarbons having up to 10 carbon atoms, primary and secondary $C_1$-$C_8$ alcohols, $C_1$-$C_{10}$ primary and secondary alkyl and aryl amines, phosphorus-containing acids, $C_1$-$C_3$ organic acids, and salts of the phosphoric and organic acids.

A particularly preferred catalytic hydrogenolysis system comprises:

A. Pd/C; and

B. a hydrogen donor selected from the group consisting of cyclohexene, cyclohexediene, phosphinic acid, sodium phosphinate, triethylammonium formate, ammonium formate, and tetralin, more preferably ammonium formate.

A solvent optionally may be present in the hydrogenolysis catalyst system. The solvent preferably comprises $C_1$-$C_4$ aliphatic alcohols, dimethyl formamide or formic acid with methanol being particularly preferred.

The halogen substituent preferably is chlorine, and substituents $R_1$, $R_2$ and $R_3$ preferably are hydrogen. The compound which is dehalogenated preferably is optically active and more preferably has the (S)-configuration.

The hydrogenolysis preferably is conducted at up to 100° C. and atmospheric pressure.

The present invention also is directed at a method for preparing a pharmaceutical composition comprising:

A. dehalogenating a compound of formula I with a catalytic hydrogenolysis system to produce a compound of formula II; and B. admixing a pharmaceutically acceptable carrier with the compound of formula II.

DETAILED DESCRIPTION OF THE INVENTION

As used herein, the term "alkyl" means straight or branched alkyl chains of 1 to 10 carbon atoms.

"Aryl" means a phenyl or naphthyl ring, or a phenyl or naphthyl ring substituted with 1-3 alkyl substituents.

"Halo" means fluoro, chloro, bromo or iodo radicals.

Also included within the scope of the invention are salts formed with pharmaceutically acceptable acids such as hydrochloric, hydrobromic, oxalic, tartaric, maleic, fumaric, methane sulfonic and the like. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Compounds of formula I have at least one asymmetrical carbon atom and, therefore, include various stereoisomers. The invention includes all such isomers both in pure form and in admixture, including racemic mixtures.

The hydrogenolysis system preferably also comprises an inert solvent, such as methanol, ethanol, isopropanol, dimethylformamide, with methanol being particularly preferred. A preferred starting composition for the hydrogenolysis system based upon the weight of starting material of formula I comprises:

A. About 25 to about 600 wt % hydrogenolysis catalyst, preferably about 75 to about 150 wt %;

B. About 60 to about 850 wt % preferably about 150 to about 250 wt % hydrogen donor; and, C. About 800 to about 4000 wt % solvent, preferably about 1500 to about 2100 wt %.

The reaction preferably is carried out under mild conditions i.e. about 15° to about 150° C. at a pressure of about 0.9 to about 4.5 atmospheres. The reaction more preferably is carried out at up to 100° C. and atmospheric pressure, in a well-stirred reaction vessel.

A particularly preferred embodiment of the present invention comprises hydrogenolysis of a compound of the formula

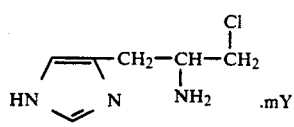
III to a compound of the formula

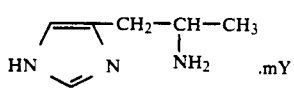
IV as set forth in detail below.

PREPARATIVE EXAMPLE 1

S-(+)4-(2-amino-3-chloropropyl)-imidazole,dihydrochloride

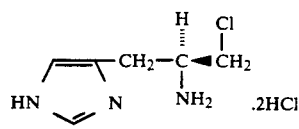

The title compound was prepared from a commercial sample of (S)-(−)-4 (2-amino-3-hydroxypropyl)-imidazole (Aldrich Chemical Co., Milwaukee, Wis., U.S.A.) according the procedures set forth by Gerhard and Schunack in Arch. Pharm. Vol. 313 pages 709-714 (1980).

S-(−)-4-(2-amino-3-hydroxypropyl)-imidazole (124.1 g) in sulfolane (2.5 kg) was heated with thionyl chloride (2.0 kg) for approximately 90 minutes The mixture was then stirred at 60° C. for 19 hours, allowed to cool to 30° C., and filtered. The precipitate from the reaction mixture was taken into 3.5 liters of boiling ethanol, charcoal treated, and filtered. The filtrate was concentrated to 1.0 liter. A solid was formed, which was filtered, washed first with ethanol, then with Et$_2$O, and dried.

The compound had the following physical properties: m.p=199°-201° C. (d.) (from ethanol); $[\alpha]_D^{26}$ =+17.6°(c=1.04, H$_2$O); $^{13}$C NMR (DMSO-d$_6$): 134 (C-2), 127 (CH$_2$), 118 (C-5), 50 (CH$_2$Cl), 44 (CHNH$_2$), 25 (CH$_2$); MS: 160 (2, M+), 110 (14), 82 (90), 81 (86), 80 (12), 78 (38), 55 (18), 54 (21), 44 (6), 43(15), 42 (19).

EXAMPLE 1

(R)-(−)4-(2-aminopropyl)-imidazole monohydrochloride

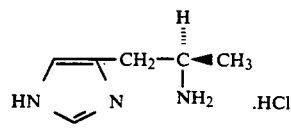

To a stirred solution of the product of Preparative Example 1 (9.6 g, 41 mmol) in dry methanol (240 mL) under nitrogen were added 10% Pd/C (12.0 g) and anhydrous ammonium formate (20.5 g, 325 mmol). The resulting mixture was refluxed under nitrogen for three hrs. The cooled mixture was filtered through diatomaceous earth, and the mixture of filter aid and catalyst was washed with methanol (200 mL), dichloromethane-methanol (1:1 by vol, 200 mL), and dichloromethane (800 mL). The combined filtrates deposited a precipitate which was removed by filtration, washed with dichloromethane, and discarded. Combined filtrates again gave a precipitate which was similarly removed, washed, and discarded. When no more precipitate formed on dilution of the combined filtrates with dichloromethane, solvents were evaporated to give the unpurified title compound (6.2 g), as a foam having the following physical properties $^1$H NMR (200 MHz, DMSO-d$_6$): 7.70 (s, 1H, H-2), 7.0 (s, 1H, H-4), 3.41 (sextet, 1H, CH(Me)NH$^+$$_3$), 2.87 (dd, 1H, $J_{A\text{-}B}$=14.5, $J_{A\text{-}CH}$=5.6, CH$_a$H$_B$), 2.70 (dd, 1H, $J_{A\text{-}B}$=14.5, $J_{B\text{-}CH}$=8.0, CH$_A$H$_B$). 1.16 (d, 3H, J=6.3, CH$_3$); $^{13}$C NMR: 17.3 (CH$_3$), 30.8 (CH$_2$), 46.4 (CHNH$^+$$_3$), 115.6 (C-5), 132.5 (C-4), 132.4 (C-2); MS(FAB): 126 (100, [M+1]$^+$).

EXAMPLE 2

(R)-(−)4-(2aminopropyl) imidazole dihydrochloride

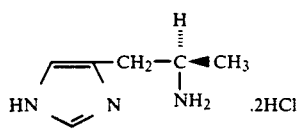

Analytically pure title compound was obtained from the title compound of Example 1 by the following procedure. An aqueous solution of the title compound of Example 1 (6.2 g) was passed through a column containing 120 g of Amberlite ® 1RA-400 (OH) ion exchange resin (Rohm and Haas Company, Philadelphia, Pa., U.S.A.) packed in H$_2$O. Removal of the solvent from the effluent under reduced pressure gave the free base (3.87 g), which was dissolved in absolute EtOH (50 mL) and was cooled in an ice bath. Saturated ethanolic HCl (70 mL) was added, after which the title compound (6.0 g) was recrystallized from 2-PrOH-Me$_2$CO, m.p. 174°–176° C.

Starting compounds where the aliphatic substituent is other than 2-amino-3-chloropropyl may be prepared by methods analagous to that set forth in Preparative Example 1 and by other methods well known in the art.

Dehalogenated compounds within the scope of compound II prepared from compounds of generalized structure I where the alkyl substituent is other than 2-aminopropyl may be prepared generally by following the methods of Examples 1 and 2 above.

Pharmaceutical formulations utilizing dehalogenated compounds prepared in accordance with the present invention are set forth below.

PHARMACEUTICAL DOSAGE FORM EXAMPLES

EXAMPLE 3

Tablets

| No. | Ingredient | mg/tablet | mg/tablet |
|---|---|---|---|
| 1. | Active Compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix item nos. 1 and 2 in suitable mixer for 10–15 minutes. Granulate the mixture with item no 3. Mill the damp granules through a coarse screen (e.g., ¼", 0.63 cm) if necessary. Dry the damp granules. Screen the dried granules if necessary and mix with item no. 4 and mix for 10–15 minutes. Add item no. 5 and mix for 1–3 minutes. Compress the mixture to appropriate size and weight on a suitable tablet machine.

EXAMPLE 4

Capsules

| No. | Ingredient | mg/capsule | mg/capsule |
|---|---|---|---|
| 1. | Active Compound | 100 | 500 |
| 2. | Lactose USP | 106 | 123 |
| 3. | Corn Starch, Food Grade | 40 | 70 |
| 4. | Magnesium Stearate NF1 | 4 | 7 |
|  | TOTAL | 250 | 700 |

Method of Manufacture

Mix item nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

EXAMPLE 5

Parenteral Preparation

| Ingredient | mg/vial | mg/vial |
|---|---|---|
| Active Compound Sterile Powder | 100 | 500 |

For reconstitution add sterile water for injection or bacteriostatic water.

While the present invention has been described in connection with certain specific embodiments thereof, it will be evident to one of ordinary skill in the art that many alternatives, modifications and variations may be made. All such alternatives, modifications and variations are intended to be included within the spirit and scope of the invention.

What is claimed is:

1. A method for dehalogenating a compound of the generalized structure

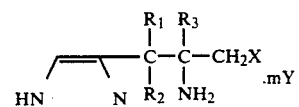

wherein R$_1$, R$_2$ and R$_3$ independently are hydrogen, or methyl, or R$_1$ and R$_3$ taken together represent a methylene, with the proviso that R$_1$, R$_2$ and R$_3$ are not all methyl;

X is halogen;

m is zero, 1 or 2; and

Y is a pharmaceutically acceptable acid, comprising contacting the compound at a pressure from about 0.9 to about 4.5 atmospheres with a catalytic hydrogenolysis system which comprises:

A. a hydrogenolysis catalyst selected from the group consisting of palladium-and nickel-containing catalysts; and, B. a hydrogen donor selected from the group consisting of unsaturated hydrocarbons having up to 10 carbon atoms primary and secondary C$_1$-C$_8$ alcohols, C$_1$-C$_{10}$ primary and secondary alkyl and aryl amines, phosphorus-containing acids, C$_1$-C$_3$ organic acids, and salts of the phosphoric and organic acids to produce a compound of the formula

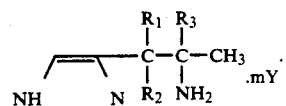

2. The method of claim 1 wherein the hydrogenolysis catalyst is supported.

3. The method of claim 2 wherein the hydrogenolysis catalyst is selected from the group consisting of Pd/C and Pd(OAc)$_2$/C.

4. The method of claim 3 wherein the hydrogenolysis system further comprises a solvent selected from the group consisting of $C_1$-$C_4$ aliphatic alcohols, dimethyl formamide and formic acid.

5. The method of claim 3 wherein the dehalogenation is conducted at mild conditions.

6. The method of claim 3 wherein the hydrogenolysis system comprises:
A. Pd/C; and
B. a hydrogen donor selected from the group consisting of cyclohexene, cyclohexediene, phosphinic acid, sodium phosphinate, triethylammonium formate, ammonium formate and tetralin.

7. The method of claim 6 wherein $R_1$, $R_2$ and $R_3$ are hydrogen.

8. The method of claim 7 wherein X is chlorine.

9. The method of claim 8 wherein the hydrogen donor is ammonium formate.

10. A method for dehalogenating a compound of the structure

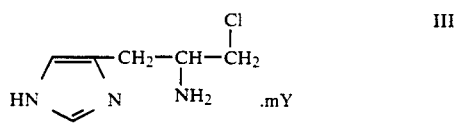

comprising contacting the compound at a pressure from about 0.9 to about 4.5 atmospheres with a catalytic hydrogenolysis system comprising:
A. Pd/C; and
B. ammonium formate at mild conditions to produce a compound of the formula

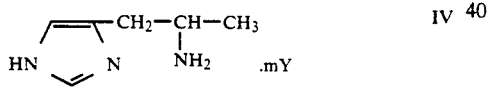

11. A method for preparing a pharmaceutical composition comprising:
A. dehalogenating a compound of the formula

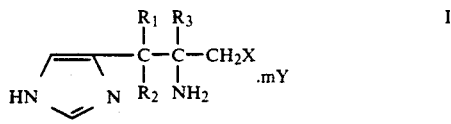

wherein $R_1$, $R_2$ and $R_3$ independently are hydrogen or methyl or $R_1$ and $R_3$ taken together may represent methylene with the proviso that $R_1$, $R_2$ and $R_3$ are not all methyl;

X is a halogen;

m is zero, 1 or 2; and

Y is a pharmaceutically acceptable acid, by
A. contacting the compound at a pressure ranging from about 0.9 to about 4.5 atmospheres with a catalytic hydrogenolysis system which comprises:
i a hydrogenolysis catalyst selected from the group consisting of palladium-and nickel-containing catalysts; and,
ii a hydrogen donor selected from the group consisting of unsaturated hydrocarbons having up to 10 carbon atoms, primary and secondary $C_1$-$C_8$ alcohols, $C_1$-$C_{10}$ primary and secondary alkyl and aryl amines, phosphorus-containing acids, $C_1$-$C_3$ organic acids and salts of the phosphoric and organic acids to produce a compound of the formula

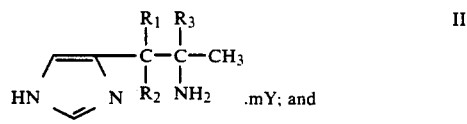

B. admixing compound II with a pharmaceutically acceptable carrier.

12. The method of claim 1 wherein the contacting of the compound with the hydrogenolysis system is conducted at about atmospheric pressure.

* * * * *